US00PP25279P3

(12) United States Plant Patent
Pavlich

(10) Patent No.: US PP25,279 P3
(45) Date of Patent: Feb. 3, 2015

(54) ***BEGONIA* PLANT NAMED 'GARDEN ANGEL PLUM'**

(50) Latin Name: ***Begonia* hybrid**
Varietal Denomination: Garden Angel Plum

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 100 days.

(21) Appl. No.: 13/986,507

(22) Filed: May 9, 2013

(65) Prior Publication Data

US 2014/0338086 P1 Nov. 13, 2014

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Annette Para
(74) *Attorney, Agent, or Firm* — Klarquist Sparkman, LLP

(57) ABSTRACT

A new and distinct form of *Begonia* plant characterized by maple-like palmately lobed leaves with showy interveinal silvering turning plum in warm temperatures, red leaf backs, a bushy habit, small clusters of large bright pink flowers in winter to early spring, hardy to USDA Z7, and excellent vigor.

1 Drawing Sheet

Botanical denomination: *Begonia* hybrid.

Variety designation: 'Garden Angel Plum'.

Parentage: *Begonia* 'Benitochiba'×*Begonia grandis* subsp. *evansiana.* Comparison to siblings *Begonia* 'Garden Angel Blush' U.S. application Ser. No. 13/986,504 and *Begonia* 'Garden Angel Silver' U.S. patent application Ser. No. 13/986,505.

BACKGROUND OF THE INVENTION

The present invention relates to a new and distinct cultivar of *Begonia,* of the family Begoniaceae, and given the cultivar name, 'Garden Angel Plum'. This plant originated from planned breeding program for a colorful series of landscape *Begonia.* The new cultivar originated from a cross between *Begonia* 'Benitochiba' (unpatented), as the seed parent, and *Begonia grandis* subsp. *evansiana* (unpatented), as the pollen parent. This selection is uniquely characterized by:

1. maple-like palmately lobed leaves with showy interveinal silvering turning plum in warm temperatures,
2. red leaf backs,
3. a bushy habit,
4. small clusters of large bright pink flowers in winter to early spring,
5. hardy to USDA Z7, and
6. excellent vigor.

Compared to the seed parent *Begonia* 'Benitochiba', an unpatented plant, the new cultivar has leaves that are palmately lobed rather than palmately compound. The new cultivar is hardy rather than being a tropical plant.

Compared to the pollen parent, *Begonia grandis* subsp. *evansiana* (an unpatented plant with the common name, Hardy *Begonia*), the new cultivar has leaves that are palmately lobed rather than no lobes and with strong interveinal silvering rather than no silvering.

Compared to *Begonia* 'Garden Angel Blush' (U.S. Plant patent application Ser. No. 13/986,504), the new cultivar is taller with the leaves colored plum in warm temperatures rather than having a plum-red violet blush.

Compared to *Begonia* 'Garden Angel Silver' (U.S. Plant patent application Ser. No. 13/986,505), the leaves of the new cultivar have interveinal silvering that turns plum in warm temperatures rather than staying silver.

The new variety has been reproduced only by asexual propagation (cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 9-month-old plant with flowers growing in a one gallon container in January in a warm greenhouse in Canby, Oreg.

DETAILED PLANT DESCRIPTION

The following is a detailed description of the new *Begonia* cultivar based on observations of 4-month-old specimens grown in one gallon containers inside a warm greenhouse in March in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The *Royal Horticultural Society Colour Chart,* $5^{th}$ edition.

Plant:

*Type.*—Herbaceous rhizomatous perennial.
*Form.*—Caulescent, shrubby.
*Cold hardiness.*—USDA Zone 7.

*Size.*—Grows to 34.5 cm tall and 33 cm wide.
*Vigor.*—Excellent.

Stem:
*Type.*—Upright.
*Size.*—Grows to 24 cm long and 8 mm wide.
*Internodes.*—From 2 cm to 8 cm long.
*Surface.*—Pubescent.
*Color.*—Greyed Purple 187A.

Leaf:
*Type.*—Simple.
*Arrangement.*—Alternate.
*Shape.*—Broadly ovate.
*Lobing/division.*—5 to 6 main palmate lobes.
*Margins.*—Serrate.
*Venation.*—Palmate, Black 202A on topside, bottom side Greyed Purple 187A.
*Apex.*—Acuminate.
*Base.*—Oblique.
*Blade size.*—Grows to 13.5 cm wide and 14 cm long.
*Surface texture.*—Pubescent on top and bottom.
*Stipules.*—Deciduous, ovate-lanceolate, grows to 18 mm long and 7 mm wide, papery, translucent, glabrous on both sides, Greyed Purple 184A.
*Petiole description.*—Grows to 10 cm long and 5 mm wide, pubescent, Greyed Brown N199A.
*Leaf color.*—Top side between Purple N77B except along veins where Black 202A, lightening to silver, Black 202C, with dark veins Greyed Green 189B in cold; bottom side for all leaves Greyed Purple 187A.

Inflorescence:
*Type.*—Axillary, bisexual, cymose.
*Number of flowers per cyme.*—About 4.
*Peduncle description.*—Grows 10 cm long and 2 mm wide, glabrous, fleshy, Greyed Brown N199C; with 2 opposite, dehiscent petiolate leaf-bracts below each cyme, which grow to 4 mm wide and 16 mm long, margins entire, tip apiculate, both sides glabrous Greyed Purple 184A.
*Pedicel description.*—Grow to 21 mm long, 1.5 mm wide, fleshy, pubescent, Red 48A on staminate and pistillate flowers.
*Bloom period.*—Winter in Canby, Oreg.

Flower bud:
*Size.*—Staminate flowers 25 mm long and 26 mm wide prior to opening; pistillate flowers are 17 mm deep and 12 mm wide prior to opening.
*Color.*—Red Purple 63A on tepal area, Greyed Red 180A on ovary.

Flower:
*Type.*—Monoecious, bilaterally symmetrical.
*Pistillate flower.*—Grows to 30 mm deep and 50 mm wide overall; 5 fleshy tepals, grow to 22 mm long and 16 mm wide, broadly elliptical, tip acute, base attenuate, margins entire, glabrous on inside and pubescent on outside, Red Purple 73A on both sides; ovary to 35 mm wide and 15 mm deep, three winged, two equal and one longer, Greyed Red 180A, style 4 mm long and 3 mm wide, Orange 22A, stigma 3 branched and twisted, stigma 6 mm deep and 10 mm wide overall, Orange 26A with edges Yellow 16B.
*Staminate flower.*—12 mm deep and 53 mm wide, 4 tepals, 2 larger outer tepals grow to 28 mm long and 20 mm wide, ovate, margin entire, tip obtuse, base cuneate; inner tepals grow to 22 mm long and 11 mm wide, oblanceolate, entire, tip obtuse, base attenuate; tepals both sides Red Purple 63A; stamen many in a globular head 7 mm in diameter on staminal column 2 mm long and 1 mm wide, Red 37C; filaments thread-like and 2.5 mm long, Green Yellow 1D, anthers 1.5 mm long, anthers Yellow 15D, no pollen.
*Fragrance.*—None.
*Lastingness.*—A cyme blooms for about 4 weeks on the plant.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

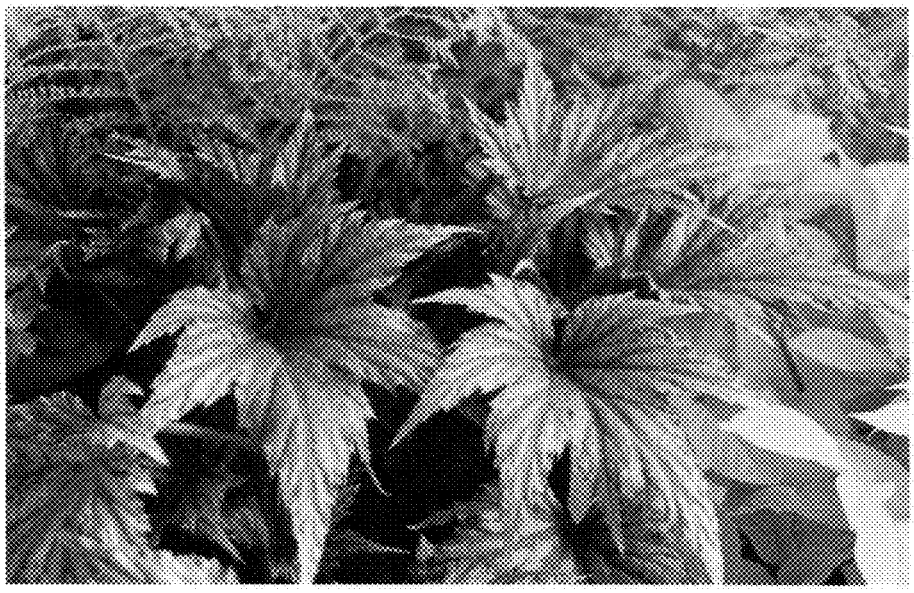

* * * * *